(12) United States Patent
Lee

(10) Patent No.: US 11,083,815 B1
(45) Date of Patent: Aug. 10, 2021

(54) SANITIZING APPARATUS

(71) Applicant: Hideko, Inc., Los Angeles, CA (US)

(72) Inventor: Sam Kwang Lee, Los Angeles, CA (US)

(73) Assignee: Hideko, Inc., Los Angeles, CA (US)

( * ) Notice: Subject to any disclaimer, the term of this patent is extended or adjusted under 35 U.S.C. 154(b) by 0 days.

(21) Appl. No.: 17/112,276

(22) Filed: Dec. 4, 2020

(51) Int. Cl.
*A61L 2/00* (2006.01)
*A61L 9/20* (2006.01)
*A61L 9/14* (2006.01)
*A61L 2/18* (2006.01)
*A61L 2/24* (2006.01)
*A61L 2/10* (2006.01)

(52) U.S. Cl.
CPC .......... *A61L 9/20* (2013.01); *A61L 2/10* (2013.01); *A61L 2/18* (2013.01); *A61L 2/24* (2013.01); *A61L 9/14* (2013.01); *A61L 2202/11* (2013.01); *A61L 2202/14* (2013.01); *A61L 2202/15* (2013.01); *A61L 2209/134* (2013.01); *A61L 2209/14* (2013.01)

(58) Field of Classification Search
CPC ..... A61L 9/20; A61L 2/10; A61L 2/18; A61L 2/24; A61L 9/14; A61L 2202/11; A61L 2202/14; A61L 2202/15; A61L 2209/134; A61L 2209/14; A61L 2/0047; A61L 9/015; A61L 2/0052; A61L 2/088; A61L 2/26; A61L 2/084; A61L 2202/25; A61L 2/0076; B01D 46/0091; B01D 2279/51; A41D 13/02; C12M 37/00; F24F 8/158; F24F 8/22; F24F 8/108; F24F 8/15; F24F 11/56; F24F 3/167; F24F 3/1603; F24F 11/30; F24F 11/62; F24F 3/16; F24F 2221/44; F24F 11/77; F24F 11/79; F24F 13/20; F24F 11/63; F24F 2006/1614; F24F 2110/30; F24F 2110/64; F24F 2120/12; Y02A 50/21
See application file for complete search history.

(56) References Cited

U.S. PATENT DOCUMENTS

| | | | |
|---|---|---|---|
| 2004/0047776 A1* | 3/2004 | Thomsen | A61L 2/10 422/186.07 |
| 2012/0040600 A1* | 2/2012 | Ortner | A41D 13/02 454/187 |
| 2014/0299672 A1* | 10/2014 | Gopalan | B05B 1/005 239/11 |
| 2019/0060492 A1* | 2/2019 | Dabney | A61L 2/084 |

\* cited by examiner

*Primary Examiner* — Xiuyu Tai
(74) *Attorney, Agent, or Firm* — Heedong Chae; Lucem, PC

(57) ABSTRACT

A sanitizing apparatus that includes a booth having a top portion, a front portion and a rear portion, with the rear portion having a set of inlets that face the front portion and the top portion having a first set of outlets such that the set of inlets and the first set of outlets are connected to each other; an air pump disposed in the rear portion configured to take in air so that the air downwardly comes out of the first set of outlets of the top portion; a filter disposed in the rear portion over the air pump wherein the filter filters the air coming out of the air pump; a ultraviolet (UV) light source disposed in the rear portion over the air pump; and a sanitizing solution spray unit installed on the front portion for spraying a sanitizing solution towards the rear portion to a user.

20 Claims, 11 Drawing Sheets

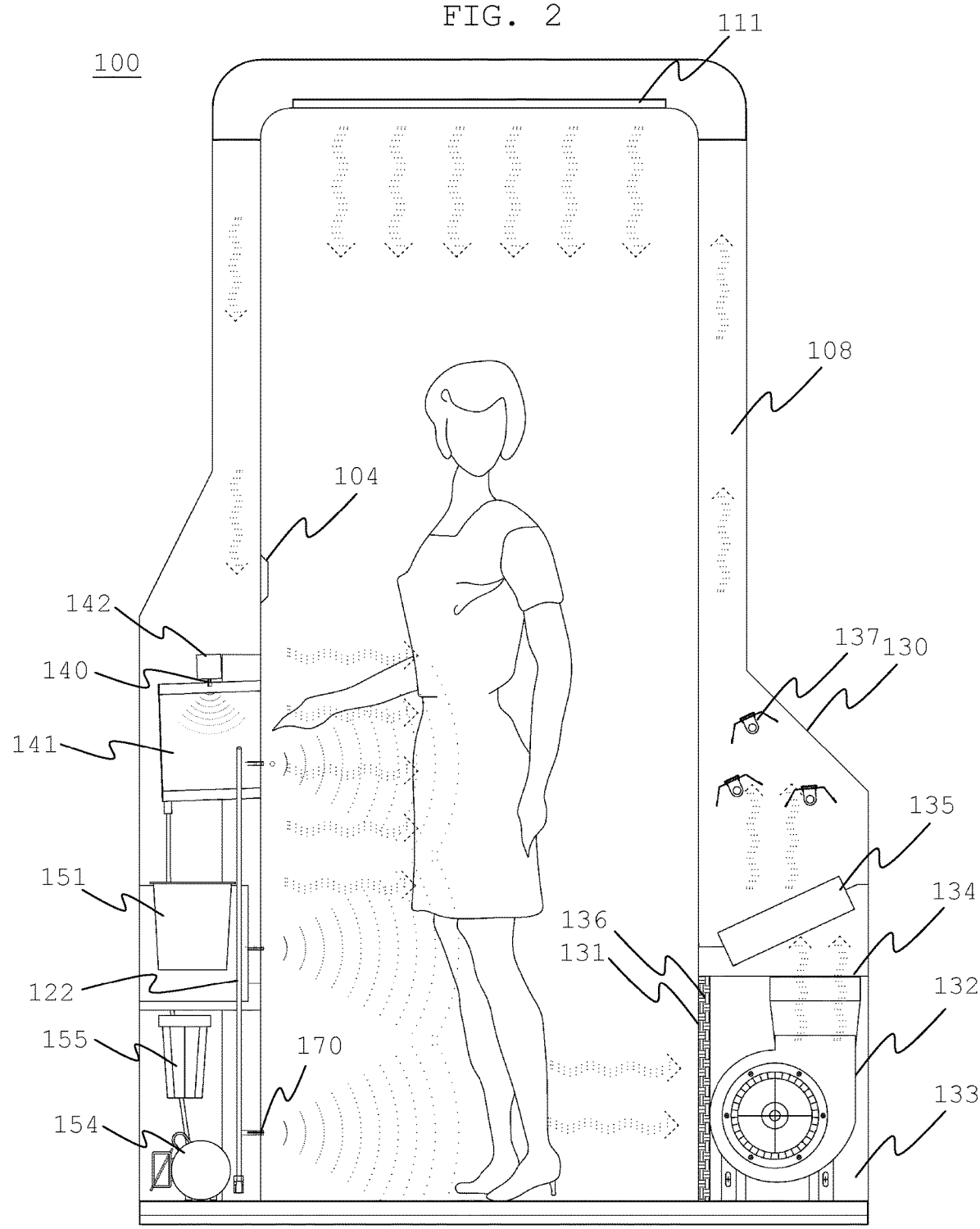

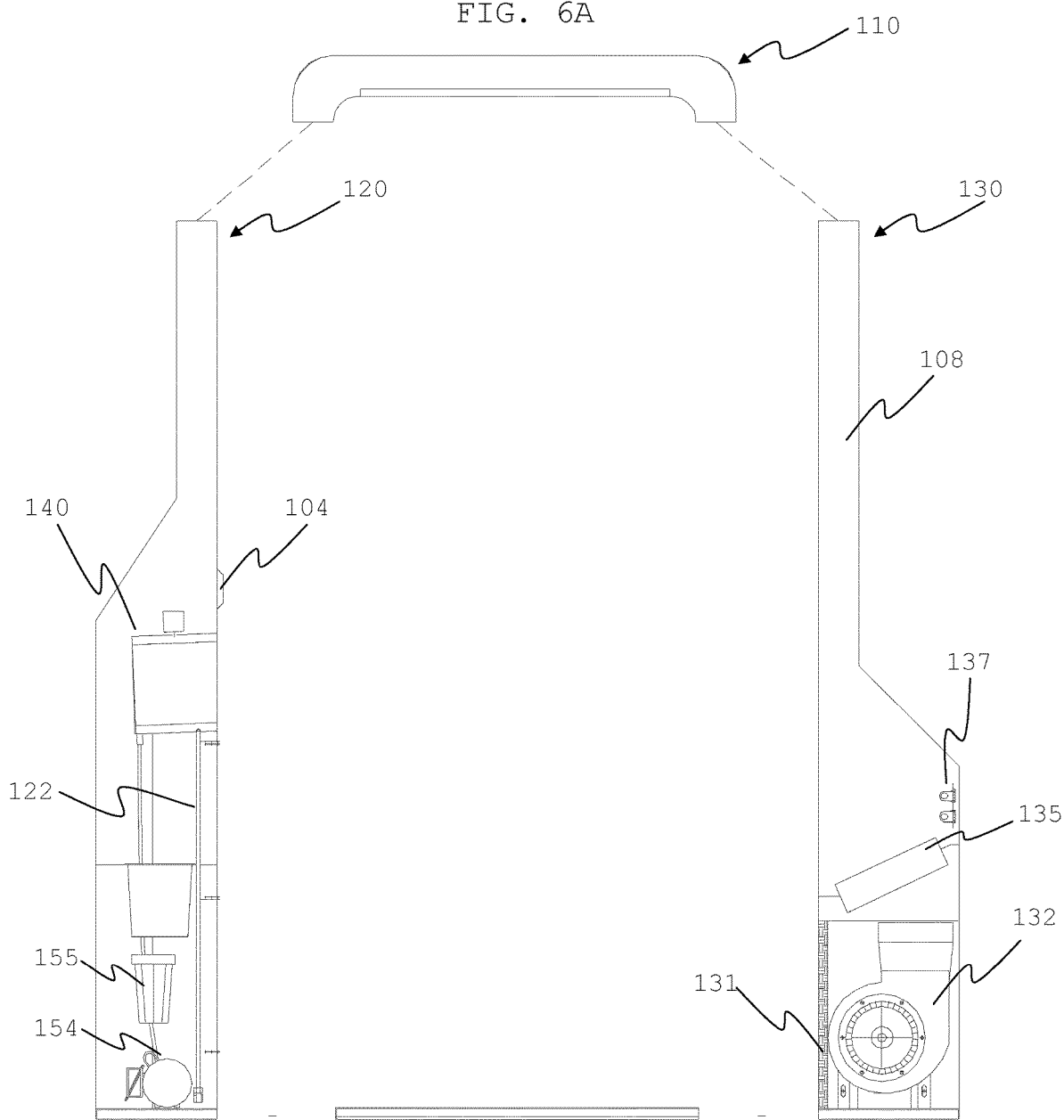

SANITIZING APPARATUS

FIELD OF THE INVENTION

The present invention relates to a sanitizing apparatus, and more particularly, a sanitizing apparatus for cleaning and disinfecting a user.

BACKGROUND OF THE INVENTION

Emerging pathogens that include bacteria and viruses may cause illness and possibly death as well as potentially being highly communicable to the extent that such pathogens may give rise to new pandemics. Since human beings can travel across a country by land or half-way around the world by air within a day via various modes of transportation, human beings are more mobile than ever. This increased mobility provides the means for the spread of various infectious vectors, some of which may give rise to deadly epidemics and pandemics. Whether by trains, planes, or boats, commercial modes of these transportation options may require security or entryway gates for their customers to pass through. Oftentimes, customers are clustered within buildings while waiting to pass through such gates. These gates often lack any type of cleaning or disinfecting features, as these gates (particularly security gates) are more often designed with the aim of detecting potential contraband items on persons passing through them. If cleaning or disinfecting features are implemented to such gates, such features may prove to be inefficient and slow, which might negate the high-throughput screening required to keep the security or entryway lines moving at an orderly pace. Therefore, there is a need for a sanitizing apparatus to work in conjunction with, or be placed at any point prior to, these gates.

Therefore, to solve the above problems, various embodiments of a sanitizing apparatus are provided, as there is a need for a device that accomplishes this goal. This invention is directed to solve these problems and satisfy the long-felt need.

SUMMARY OF THE INVENTION

The present invention contrives to solve the disadvantages of the prior art. The present invention provides a sanitizing apparatus for cleaning or disinfecting a user.

The object of the invention is to provide a sanitizing apparatus for cleaning or disinfecting which includes a booth having a top portion, a front portion and a rear portion, wherein the rear portion has a set of inlets and the top portion has a first set of outlets such that the set of inlets and the first set of outlets are connected to each other through a hollow inside of the rear portion and a hollow inside of the top portion, wherein the set of inlets faces the front portion; an air pump disposed in the rear portion wherein the air pump takes air in through the set of inlets and sends the air upwardly through the hollow inside of the rear portion to the hollow inside of the top portion so that the air downwardly comes out of the first set of outlets of the top portion; a filter disposed in the rear portion over the air pump wherein the filter filters the air coming out of the air pump; a ultraviolet (UV) light source disposed in the rear portion over the air pump wherein the UV light source emits UV light for disinfecting the air coming out of the air pump; and a sanitizing solution spray unit installed on the front portion for spraying a sanitizing solution towards the rear portion to a user.

Another object of the invention is to provide a sanitizing apparatus for cleaning or disinfecting, which includes a booth having a set of inlets and a set of outlets wherein the set of inlets and the set of outlets are connected to each other by hollow inside of the booth; an air pump disposed in the booth wherein the air pump takes air in through the set of inlets and sends the air through the hollow inside of the booth so that the air comes out of the set of outlets of the booth; a filter disposed in the booth over the air pump wherein the filter filters the air coming out of the air pump; a ultraviolet (UV) light source disposed in the booth over the air pump wherein the UV light source emits UV light for disinfecting the air coming out of the air pump; a sanitizing solution spray unit installed on the booth for spraying a sanitizing solution to a user; and a hand sanitizer dispensing unit disposed in the booth for dispensing a hand sanitizer.

The advantages of the present invention are: (1) increased effectiveness in cleaning/sanitization/disinfection due to a combination of an air shower, sanitizing mist and hand sanitizer; (2) arch-shaped, walk-through booth allows fast and easy-to-access sanitizing method, and such a booth may be installed in front of security gates or in front of entrances (or leading up to entrances) of buildings, airplanes, boats, etc., and, with respect to airplanes, the sanitizing apparatus may be installed in front of jetways that lead passengers into their airplanes prior to taking off since air travel has been shown to be a major factor in the spread of certain illnesses, some of which may lead to epidemics and pandemics; (3) the slanted configuration of the filter facilitates the air flow such that the air can be easily spread towards the top portion and the front portion; (4) since the air passage that is narrower in the upper part than the lower part of the rear portion, the air movement is slower in the lower part, thereby allowing enough time for the UV light (which is disposed in the lower part) to sterilize the air; (5) the sanitizing solution is sprayed from both flanges toward the user to clean/disinfect a large part of the front of the user; (6) the sanitizing solution sprayed from both flanges work like a "curtain" which prevents any germs, virus, dust, etc. from spreading or traveling sideways; (7) the air is discharged more strongly from the top than from the front so any dusts washed off the user may sink to enter the air inlet at the bottom and to eventually be filtered out by the filter for effective sanitizing and disinfecting; (8) the range of mist spray will be limited to below the respiratory tract of an average height human so the mist can be sprayed directly to the user without raising any health concerns, and in compliance with any local health regulations; (9) usage of two filters (prefilter and HEPA filter) leads to more effective filtering; (10) the hand sanitizing/air shower and sanitizing solution spray may be configured to be operated by different sensors so when one function fails, the other function will still work; (11) the filters are easily replaceable due to the construction of the inlet panel, which allows for quick replacement of the filters and very short downtimes; and (12) liquid level indicators allow one to easily figure out when to refill the sanitizing solutions.

Although the present invention is briefly summarized, the fuller understanding of the invention can be obtained by the following drawings, detailed description and appended claims.

BRIEF DESCRIPTION OF THE DRAWINGS

These and other features, aspects and advantages of the present invention will become better understood with reference to the accompanying drawings, wherein:

FIG. 2 shows a side view of a sanitizing apparatus according to embodiments of the present invention;

FIGS. 6A and 6B show exploded side and perspective views respectively of a sanitizing apparatus according to embodiments of the present invention;

DETAILED DESCRIPTION OF EMBODIMENTS OF THE INVENTION

Reference will now be made in detail to the preferred embodiments of the present invention, examples of which are illustrated in the accompanying drawings, which form a part of this disclosure. It is to be understood that this invention is not limited to the specific devices, methods, conditions or parameters described and/or shown herein, and that the terminology used herein is for the purpose of describing particular embodiments by way of example only and is not intended to be limiting of the claimed invention.

Also, as used in the specification including the appended claims, the singular forms "a", "an", and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value.

Similarly, when values are expressed as approximations, by use of the antecedent "about", it will be understood that the particular value forms another embodiment.

Figure 1A:
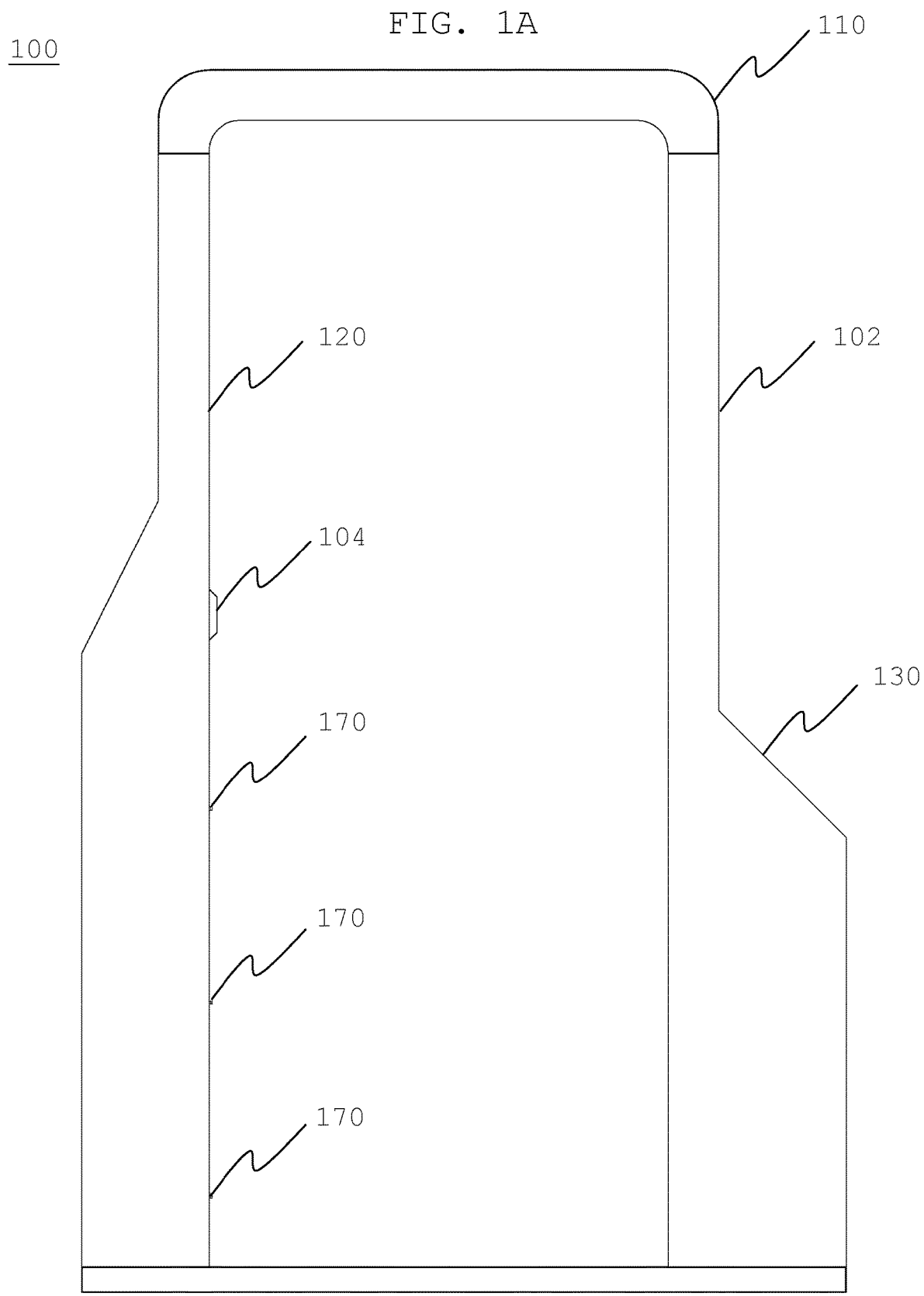
FIGS. 1A and 1B show side views of a sanitizing apparatus according to embodiments of the present invention.
Figure 1B:
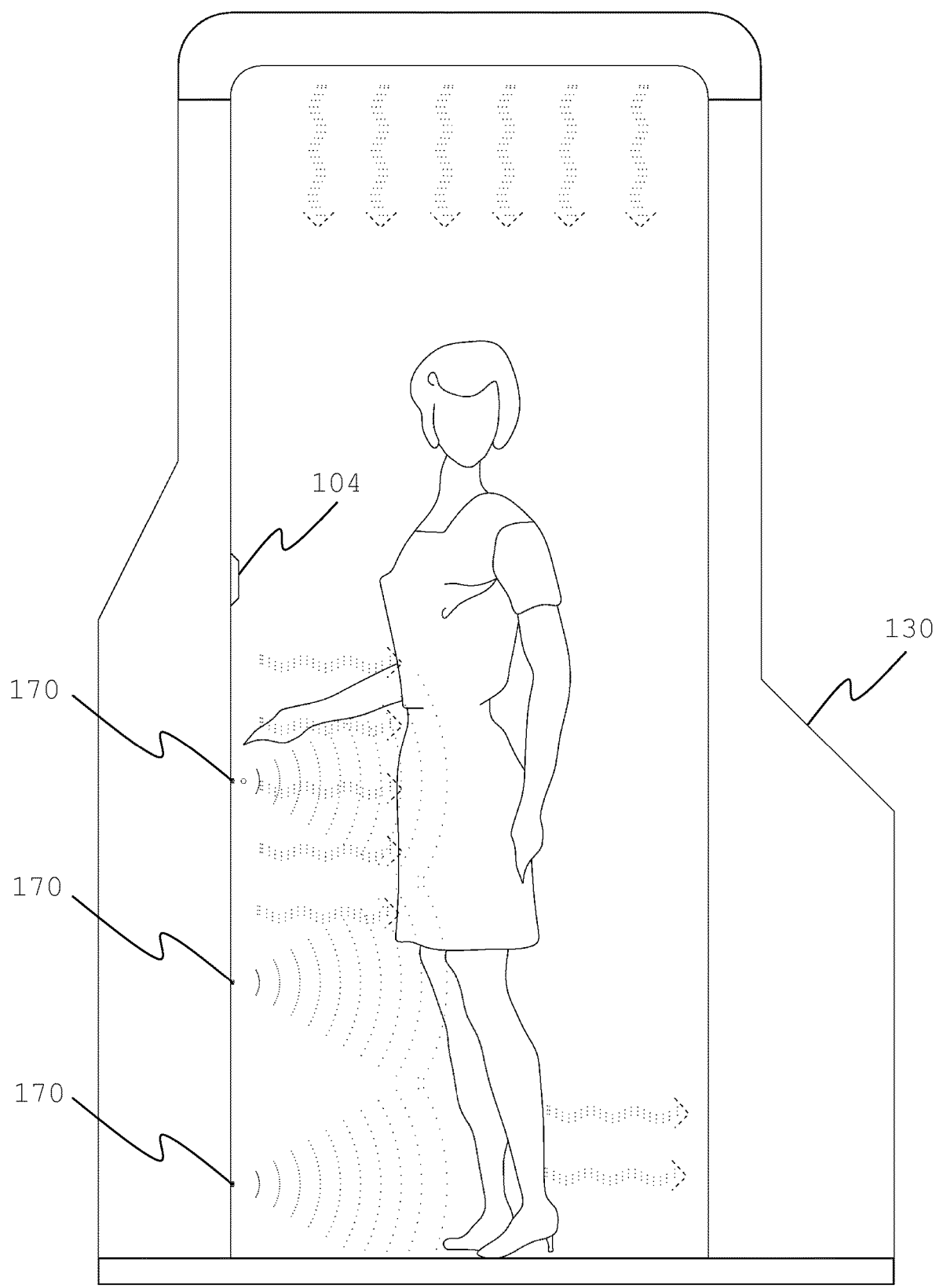
Figure 3:
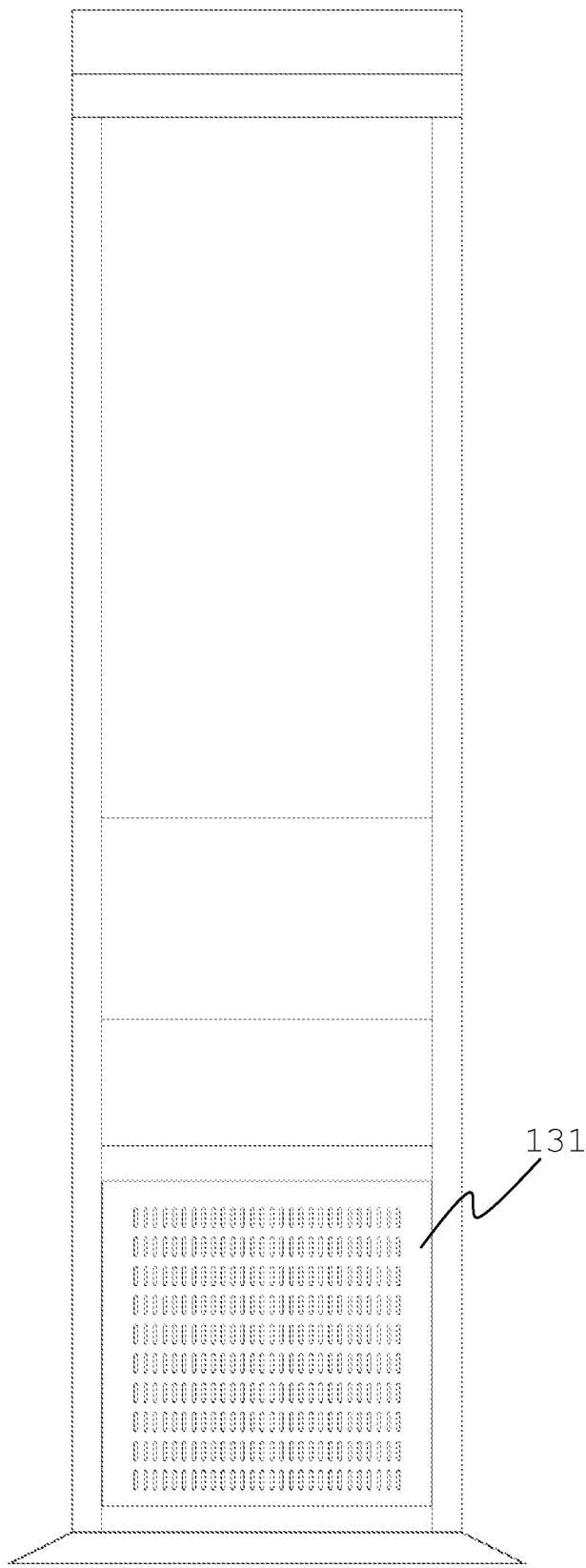
FIG. 3 shows a rear view, from a user's point of view, of an inside of a sanitizing apparatus according to embodiments of the present invention.

A sanitizing apparatus (100) for cleaning or disinfecting, as shown in FIGS. 1A, 1B, and 2, includes a booth (102) having a top portion (110), a front portion (120) and a rear portion (130); an air pump (132) disposed in the rear portion (130); a filter (135) disposed in the rear portion (130) over the air pump (132); a ultraviolet (UV) light source (137) disposed in the rear portion (130) over the air pump (132); and a sanitizing solution spray unit (122) installed on the front portion (120) for spraying a sanitizing solution towards the user and the rear portion (130). As shown in FIGS. 1B and 2, the user stands between the front portion (120) and the rear portion (130) of the sanitizing apparatus. As shown in FIGS. 2 and 3, the rear portion (130) has a set of inlets (131) and the top portion (110) has a first set of outlets (111) such that the set of inlets (131) and the first set of outlets (111) are connected to each other through a hollow inside of the rear portion (130) and a hollow inside of the top portion (110). The set of inlets (131) may be constructed as a plurality of through-holes on a removable panel as shown in FIG. 3. As shown, the set of inlets (131) faces the front portion (120).

As shown in FIG. 2, the top, front, and rear portions (110, 120, 130) are constructed to be hollow internally and communicative with respect to each other, which forms an air passage (108) to permit internal air flow through the respective portions, the air flow preferably driven by an air pump (132). As shown, the air pump (132) is disposed in the rear portion (130) of the sanitizing apparatus (100). More specifically, the air pump (132) is disposed in an air chamber (133). The air chamber (133) includes a duct (134) so that the air output from the air pump (132) is directed through the duct (134) and into the portion of the air passage (108) in the rear portion (130). The air pump (132) is configured to take air in through the set of inlets (131) and send the air upwardly through the hollow inside of the rear portion (130) to the hollow inside of the top portion (110) so that the air downwardly comes out of the first set of outlets (111) of the top portion (110). A filter (135) disposed above the air pump (132) filters the air coming out of the air pump (132). Preferably, the filter (135) is a high efficiency particulate air (HEPA) filter and is disposed either outside or inside of the air chamber so long as the air output from the air pump (132) passes through the filter (135). For disinfecting purposes, the UV light source (137), with respect to the path of the air flow from the air pump (132), is preferably disposed after the filter (135). Alternatively, the UV light source is disposed prior to the filter (135), although this configuration is less preferred because the air at this juncture will not be filtered by the filter (135). The UV light source (137) is configured to emit UV light, to disinfect the air coming out of the air pump (132) that has been filtered by the filter (135). Preferably, the UV light source (137) is a UV-C lamp. There is at least one UV light source (137) disposed in the sanitizing apparatus (100) to disinfect the air flow, preferably a plurality of UV light sources (137) as shown in FIG. 2.

Figure 4:
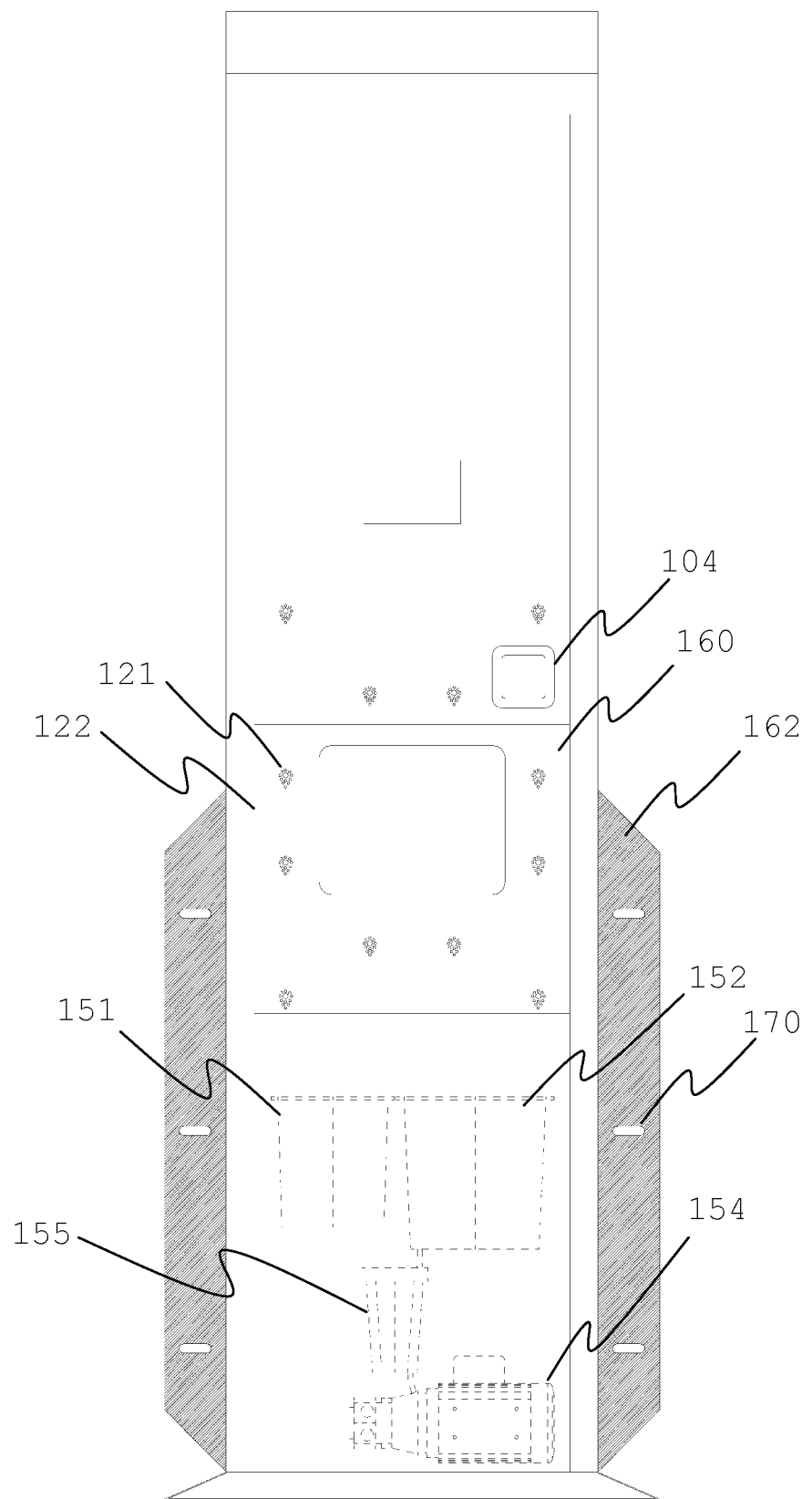
FIG. 4 shows a front view, from a user's point of view, of an inside of a sanitizing apparatus according to embodiments of the present invention.

Also shown in FIG. 2, the sanitizing apparatus (100) may further include a hand sanitizer dispensing unit (140) for dispensing a hand sanitizer. The hand sanitizer dispensing unit (140) is disposed in the front portion (120). As shown in FIG. 4, the hand sanitizer dispensing unit (140) includes a hand sanitizing compartment (141) to insert user's hands and a hand detection sensor (142). The hand detection sensor (142) detects the presence of a user's hand and is located within the hand sanitizing compartment (141). The hand detection sensor (142) may be a motion sensor configured to detect the presence of the user's hand in the hand sanitizing compartment (141) by monitoring the hand sanitizing compartment (141) for movement of the user's hand into the compartment (141) about a location where the hand sanitizer dispensing unit (140) may dispense the hand sanitizer onto the user's hand. When the hand detection sensor (142) detects the user's hand, the hand detection sensor (142) signals to the hand sanitizer dispensing unit (140) to initiate dispensing of the hand sanitizer.

The sanitizing apparatus (100) shown in FIGS. 2 and 4 may further include a first container (151) for storing the hand sanitizer for dispensing the hand sanitizer. With regards to the hand sanitizer, it is preferred that the hand sanitizer will contain at least 62% or more ethanol. Also preferably, the first container (151) is disposed in the front portion (120). The sanitizing apparatus (100), as shown, may further include a second container (152) for storing the sanitizing solution and a pump (154) to provide the pressure for spraying the sanitizing solution. The pump (154) is motorized and is disposed in the front portion (120) and the second container (152) is disposed in the front portion (120) over the pump (154). Furthermore, the sanitizing apparatus (100) may further include a compartment to store the first and second containers (151, 152) therein. Preferably, the pump (154) is disposed in the front portion (120) below the second container (152). Additionally, as shown in FIG. 4, a filter (155) may be disposed between the second container (152) and the pump (154) such that any grounds, dirt, or impurities may be filtered out from the sanitizing solution before the spraying of the sanitizing solution. Accordingly, the filter (155) may prevent clogging of any tubes and/or nozzles used for pumping and spraying the sanitizing solution.

With regards to the sanitizing solution that is to be sprayed towards the body of the user, a slightly acidic hypochlorous acid is preferred. The slightly acidic hypochlorous acid aqueous solution has a pH range between 5-6.5, and a concentration of available chlorine between 10-30 ppm. The slightly acidic hypochlorous acid aqueous solution exhibits strong sterilizing properties even with a relatively low concentration of available chlorine, and it is ecofriendly since it does not generate chloroform even when in contact with organic matter. This preferred solution is distinguishable from sodium hypochlorite (commonly known as bleach). However, the efficacy of using hypochlorous acid for sterilization decreases after more than two weeks because the chlorine concentration is reduced as time passes. Therefore, if hypochlorous acid aqueous solution is used as the sanitizing solution, it must be replaced at least once every ten days.

As shown in FIGS. 2 and 4, the sanitizing apparatus (100), the front portion (120) includes a second set of outlets (121) which is directed toward the rear portion (130). The set of inlets (131) and second set of outlets (121) are connected to each other through the air passage (108) formed by the hollow inside of the rear portion (130), the hollow inside of the top portion (110), and a hollow inside of the front portion (120). The air pump (132) takes air in through the set of inlets (131) and sends the air upwardly through the hollow inside of the rear portion (130) to the hollow portion of the top portion (110) and then to the hollow portion of the front portion (120) so that the air comes out of the second set of outlets (121) towards the rear portion (130). In this configuration, air travels within the air passage (108) from the rear portion (130) to the top portion (110) with some of the air passing through the set of outlets provided on the top portion (110). Thereafter, the remaining air in the air passage (108) travels to the front portion (120) where the air then passages through the set of outlets provided on the front portion (120).

From the viewpoint of the user, this configuration allows air to be blown downwardly onto the head of the user from the direction of the top portion (110) and then blown (depending on the user's position) towards the face, neck, and/or chest area(s); the back of the head, back of the neck, and/or back area(s); or the side of the head, side of the neck, and/or side of an arm area(s). Preferably, during normal operation, the blowing of the air is initiated by the hand detection sensor (142) disposed in the front portion (120) of the booth (102). Since the user has to face towards the front portion (120) to insert their hand in the hand sanitizing compartment (141), the user will likely be facing towards the front portion (120) when the air blowing is initiated. Therefore, during normal operation of the sanitizing apparatus (100), the air will be blown downwardly from the top portion (110) to the user standing below it and blown towards the user standing in front of the front portion (120).

The front portion (120) of the sanitizing apparatus (100) may include a front chamber (160) and a pair of flanges (162). As shown in FIG. 4, each of the flanges (162) extends laterally from the front chamber (160). As shown, the second set of outlets (121) is disposed on the front chamber (160). The sanitizing solution spray unit (122) includes a plurality of spray nozzles (170) installed on the flanges (162). When the sanitizing apparatus (100) is operative and after a user stands within it, sanitizing solution is sprayed from both flanges (162) towards the user, and towards the rear portion (130), to clean/disinfect a large portion of the front of the user.

Likewise, with the blowing of the air to the user, the spraying of the sanitizing solution from the spray nozzles (170) is initiated by the user placing their hand into the hand sanitizing compartment (141) such that the hand detection sensor (142) detects the user's hand inside of the hand sanitizing compartment (141), which means that the user is highly likely to be standing inside of the booth (102) area and positioned to be cleaned or disinfected from the operation of the sanitizing apparatus (100).

As shown in FIGS. 1A-B, 2, and 4, the sanitizing apparatus (100) may further include a contactless switch (104) configured to detect the user's hand movement in proximity for initiating spraying of the sanitizing solution to the user. The sanitizing apparatus (100) may further include a user detection sensor (106) to detect presence of the user for initiating air circulation from the set of inlets (131) (inflow into the rear portion (130)) to the first set of outlets (111) (outflow from the front portion (120)) by the air pump (132). The detection sensor (106) may be a weight sensor, infrared sensor, or the like that is configured to detect the user standing within the booth (102). If the user detection sensor (106) is an infrared sensor, then it may be installed in the top portion (110) and point down towards the bottom portion. This infrared sensor will then wait for the user to break its beam when the user steps into the booth (102); breaking the infrared beam of the infrared sensor will produce a signal from the infrared sensor to initiate the air circulation described above. If the detection sensor (106) is a weight sensor, the weight sensor will be disposed at a bottom portion in the booth (102) whereupon the weight sensor detects the weight from the user's foot when the user steps onto the bottom portion of the booth (102). When the weight sensor detects this event, then the weight sensor will signal to initiate the air circulation described above.

Figure 5:
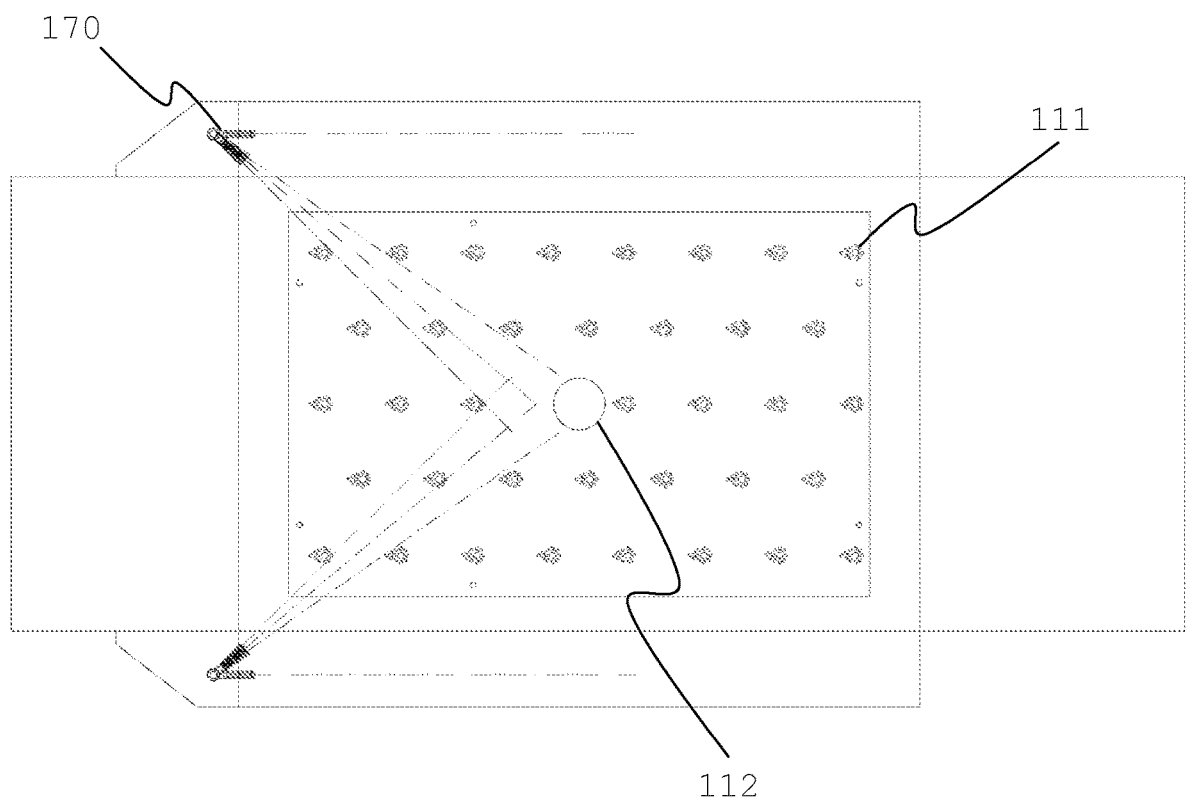
FIG. 5 shows a view, when the user is staring upwards, of an inside of a sanitizing apparatus according to embodiments of the present invention.

FIG. 5 shows a view of a bottom-side of the top portion (110) of the booth (102). As shown, a light-emitting diode (LED) (112) is installed in the bottom-side of the top portion (110). Preferably, the LED (112) is programmed to turn on when the hand detection sensor (142) detects the user's hand. Alternatively, the LED (112) can be programmed to turn on once the user detection sensor (106) detects the user, or at least part of the user, in the booth (102). For example, when the user steps into the booth (102), the user's foot will likely step on the bottom portion of the booth (102). If the bottom portion of the booth includes a weight sensor as the user detection sensor (106), the weight sensor will detect the user's foot stepping onto the bottom portion of the booth (102) and produce a signal to turn on the LED (112). Likewise, when the user detection sensor (106) is an infrared sensor whereupon breaking the infrared beam by stepping into booth (102) will produce a signal from the infrared sensor to turn on the LED (112).

With regards to the air passage (108) of the sanitizing apparatus (100), FIG. 2 shows that the air passage (108) in the rear portion (130) is narrower in an upper part of the rear portion (130) than a lower part of the rear portion (130). This configuration permits faster air movement in the upper part of the rear portion (130) than in the lower part of the rear portion (130), which leads to air more strongly being discharged from the top portion (110) than from the front portion (120). Also shown, the filter (135) is slanted towards the user and the UV light source (137) is disposed on an outer side wall of the rear portion (130) right over the filter (135). Preferably, to properly fit in the air pump (132), the filter's (135) length is greater than the width. From the side view as shown in FIG. 2, the placement of a plurality of the UV light sources (137) in the rear portion (130) of the booth (102) forms an acute trapezoid where the UV light source (137) is preferably disposed on the shorter base of the trapezoid to sanitize more air with wide angle.

The air pump (132) may include a prefilter (136) installed on the set of inlets (131) as shown in FIG. 2. The set of inlets (131) may be a part of an inlet panel with the set of inlets (131) being a plurality of through-holes as shown in FIG. 3. The prefilter (136) may be installed on the panel. As shown, the outer edge of the inlet panel has "E-shaped" frames on the side directed towards the rear portion (130) of the booth (102) such that the prefilter (136) can be stably fitted therein. Therefore, during maintenance of the sanitizing apparatus (100), the prefilter (136) can be easily removed and replaced with either a cleaned prefilter (136) or a new prefilter (136), fitted into the frames of the inlet panel with minimal downtime. The inlet panel will then be fitted back to the rear portion (130) of the booth (102) so that normal operation of the sanitizing apparatus (100) may resume. The inlet panel may be coupled to the rear portion (130) of the booth (102) by a hinge. Alternatively, the inlet panel may be removably coupled to the rear portion (130) of the booth (102) by a plurality of screws (not shown).

Any dust washed off from the user due to the overhead air dispensed from the direction of the top portion (110) will sink to the bottom. Dust washed off from the user due to the air dispensed from the direction of the front portion (120) will go towards the rear. Since the sunken dust with any infectious vector(s) will go through the set of inlets when the air pump (132) is operating, this sunken dust will be eventually filtered out by the prefilter (136) and the filter (135). This double filtering will effectively from the dust and any infectious vectors that are residing thereon to be less of a health concern. For any dust or germs that may travel or spread sideways from inside of the booth (102) to outside of the booth (102) (and thus spread outside of the sanitizing apparatus (100)), the sanitizing solution spray unit (122) sprays sanitizing solution to about the sides of the user, which then would wash out the sideways-spreading dust or germs. More specifically, the sanitizing solution is sprayed from both sides of the front portion (120) towards the user and the rear portion (130), and the range of spray of the sanitizing solution is configured to be laterally wide enough such that a sanitizing curtain may be formed to attenuate any outside spread of germs and/or dust from the sanitizing apparatus (100). For safety reasons, the range of spray of the sanitizing solution will be limited to below the respiratory tract of an average height human so the sanitizing solution can be sprayed directly to the user.

Figure 6B:
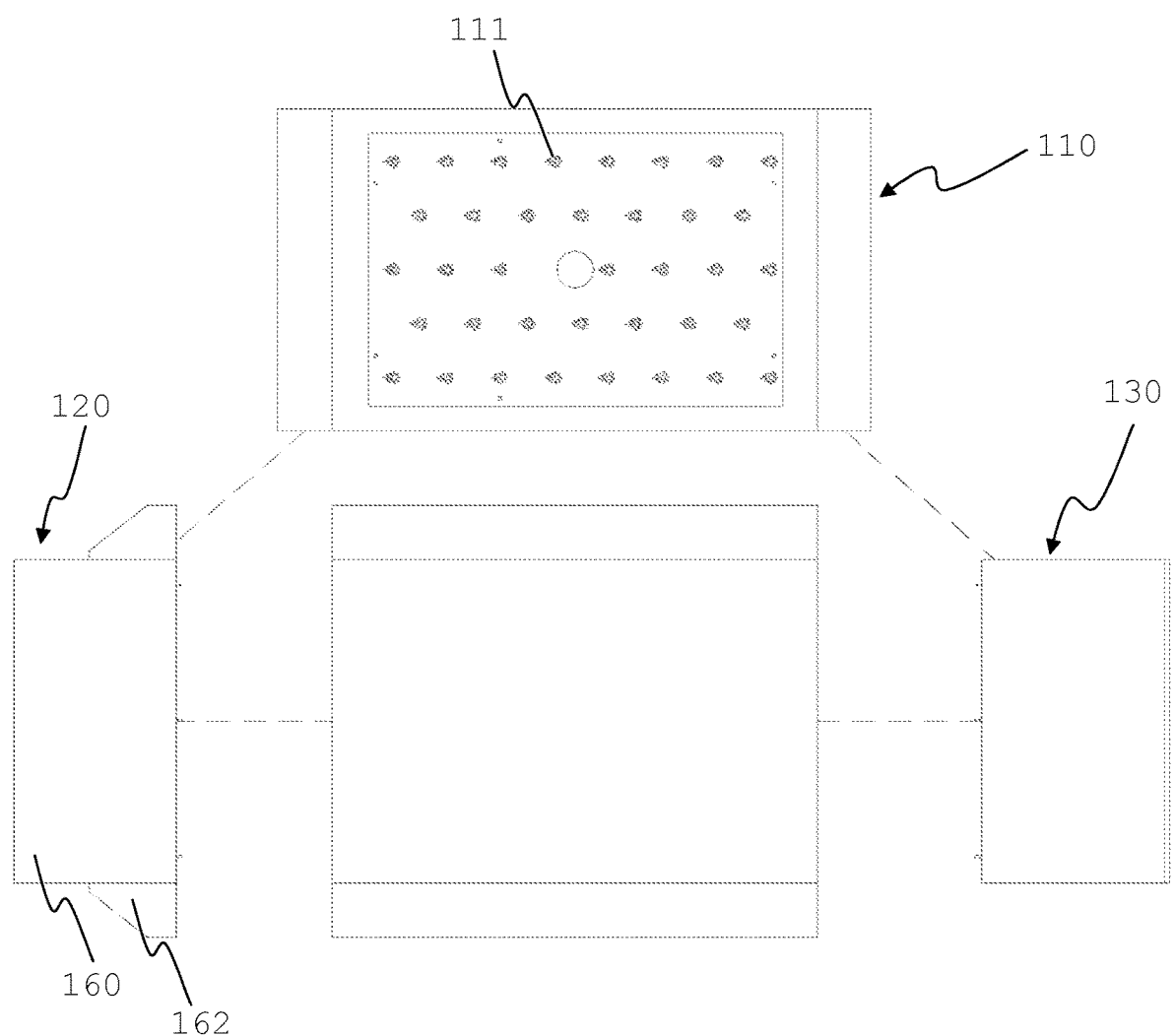

As shown in FIGS. 6A and 6B, the spraying apparatus (100) can be easily dissembled at one location for assembly in another location. The top (110), bottom, front (120), and rear portions (130) can be disassembled from each other and then reassembled with ease much like a flat pack furniture. This feature allows for easy installation and transportation of the spraying apparatus wherever it may be needed.

For easier mobility of the booth (102), a plurality of casters (fixed or swiveling types) may be attached underneath the bottom portion of the booth (102). The casters may include a locking mechanism to prevent the sanitizing apparatus (100) from moving after finding an ideal placement location. Furthermore, the casters may be solid, hollow, or pneumatically filled with air or any other fill known in the art. Alternatives to casters include rubberized tracks or adjustable glides. The rubberized tracks may be more stable than casters. The glides may be adjusted and set to contact the ground and set the bottom portion of the booth (102) to the ground when the sanitizing apparatus (100) is placed at a particular location. The glides are likely more stable than casters because the glides have the ability to set the sanitizing apparatus (100) on the ground without any gap formed between the sanitizing apparatus (100), so the user avoids have their foot trip over the bottom portion of the booth (102) due to the gap between it and the ground if casters were used.

In an alternative embodiment, a sanitizing apparatus (100) for cleaning or disinfecting, includes a booth (102) having a set of inlets (131) and a set of outlets (111) where the set of inlets (131) and the set of outlets (111) are connected to each other by hollow inside of the booth (102); an air pump (132) disposed in the booth (102) where the air pump (132) takes air in through the set of inlets (131) and sends the air through the hollow inside of the booth (102) so that the air comes out of the set of outlets (111) of the booth (102); a filter (135) disposed in the booth (102) over the air pump (132) where the filter (135) filters the air coming out of the air pump (132); an ultraviolet (UV) light source (137) disposed in the booth (102) over the air pump (132) where the UV light source (137) emits UV light for disinfecting the air coming out of the air pump (132); a sanitizing solution spray unit (122) installed on the booth (102) for spraying a sanitizing solution to the user; and a hand sanitizer dispensing unit (140) disposed in the booth (102) for dispensing a hand sanitizer.

In this second embodiment, the hand sanitizer dispensing unit (140), disposed in the booth (102), includes a hand sanitizing compartment (141) to insert user's hands and a hand detection sensor (142) configured to detect presence of a user's hand located within the hand sanitizing compartment (141) to initiate dispensing of hand sanitizer. As in the first embodiment, the hand detection sensor (142) detects the presence of a user's hand and is located within the hand sanitizing compartment (141). The hand detection sensor (142) may be a motion sensor configured to detect the presence of the user's hand in the hand sanitizing compartment (141) by monitoring the hand sanitizing compartment (141) for movement of the user's hand into the compartment (141) about a location where the hand sanitizer dispensing unit (140) may dispense the hand sanitizer onto the user's hand. When the hand detection sensor (142) detects the user's hand, the hand detection sensor (142) signals to the hand sanitizer dispensing unit (140) to initiate dispensing of the hand sanitizer.

As shown in FIG. 4, the booth (102) of the sanitizing apparatus (100) may include a side chamber (160) and a pair of flanges (162), each of which extends from the side chamber (160). The sanitizing solution spray unit (122) includes a plurality of spray nozzles (170) installed on the flanges (162). Each of the flanges (162) includes one or more spray nozzles (170) installed thereon as shown. Also shown, the set of outlets (111) is formed on the side chamber (160). As shown in FIG. 5, another set of outlets and a top portion (110) of the booth (102). Also shown is a light-emitting diode (LED) (112) installed in the top portion of the booth (102). Preferably, the LED (112) is programmed to turn on when the hand detection sensor (142) detects the user's hand.

From the viewpoint of the user, the configuration of this embodiment allows air to be blown downwardly onto the head of the user from the direction of the top portion (110) and, from the side chamber (160), the air is then blown (depending on the user's position) towards the face, neck, and/or chest area(s); the back of the head, back of the neck, and/or back area(s); or the side of the head, side of the neck, and/or side of an arm area(s). Preferably, during normal operation, the blowing of the air is initiated by the hand detection sensor (142) disposed in the booth (102). Since the user has to face towards the side chamber (160) in insert their hand in the hand sanitizing compartment (141), the user will be likely facing towards the side chamber (160) when the air blowing is initiated. Therefore, during normal operation of the air will be blown downwardly from the top portion (110) to the user standing below it and blown towards the user standing in front of the side chamber (160).

The air passage (108) in a side portion (130) of the booth (102) is narrower in an upper part of the side portion (130) than a lower part of the side portion (130). This configuration permits faster air movement in the upper part of the side portion (130) than in the lower part of the side portion (130). Also shown, the filter (135) is slanted towards the user and the UV light source (137) is disposed on an outer side wall of the side portion (130) right over the filter (135). Preferably, the filter (135) is a high efficiency particular air (HEPA) filter. Furthermore, to properly fit in the air pump (132), the filter's (135) length is greater than the width. From the side view as shown in FIG. 2, UV light source (137) may be a plurality of UV light sources (137) and the placement these UV light sources (137) in the side portion (130) of the booth (102) preferably forms an acute trapezoid where the UV light source (137) is preferably disposed on the shorter base of the trapezoid to sanitize more air at a wider angle.

Any dust washed off the user due to the overhead air dispensed from the direction of the top portion (110) will sink to the bottom. Dust washed off from the user due to the air dispensed will go towards the side portion (130). Since the sunken dust with any infectious vector(s) will go through the set of inlets (131) when the air pump (132) is operating, this sunken dust will be eventually filtered out by the prefilter (136) and the filter (135). This double filtering will effectively from the dust and any infectious vectors that are residing thereon to be less of a health concern. For any dust or germs that may travel or spread sideways from inside of the booth (102) to outside of the booth (102) (and thus spread outside of the sanitizing apparatus (100)), the sanitizing solution spray unit (122) sprays sanitizing solution to the sides of the user, which then would wash out the sideways-spreading dust or germs. More specifically, the sanitizing solution is sprayed from both sides of the front portion (120) towards the user and the rear portion (130), and the range of spray of the sanitizing solution is configured to be laterally wide enough such that a sanitizing curtain may be formed to attenuate any outside spread of germs and/or dust from the sanitizing apparatus (100). For safety reasons, the range of spray of the sanitizing solution will be limited to below the respiratory tract of an average height human so the sanitizing solution can be sprayed directly to the user.

For easier mobility of the sanitizing apparatus (100) as a whole of this embodiment, a plurality of casters (fixed or swiveling types) may be attached underneath the bottom portion of the booth (102). The casters may include a locking mechanism to prevent the sanitizing apparatus (100) from moving after finding an ideal placement location. Furthermore, the casters may be solid, hollow, or pneumatically filled with air or any other fill known in the art. Alternatives to casters include rubberized tracks or adjustable glides. The rubberized tracks may be more stable than casters. The glides may be adjusted and set to contact the ground and set the bottom portion of the booth (102) to the ground when the sanitizing apparatus (100) is placed at a particular location. The glides are likely more stable than casters because the glides have the ability to set the sanitizing apparatus (100) on the ground without any gap formed between the sanitizing apparatus (100), so the user avoids have their foot trip over the bottom portion of the booth (102) due to the gap between it and the ground if casters were used. Any other features of the first embodiment not stated in the second embodiment may be optionally included in the second embodiment.

Figure 7:
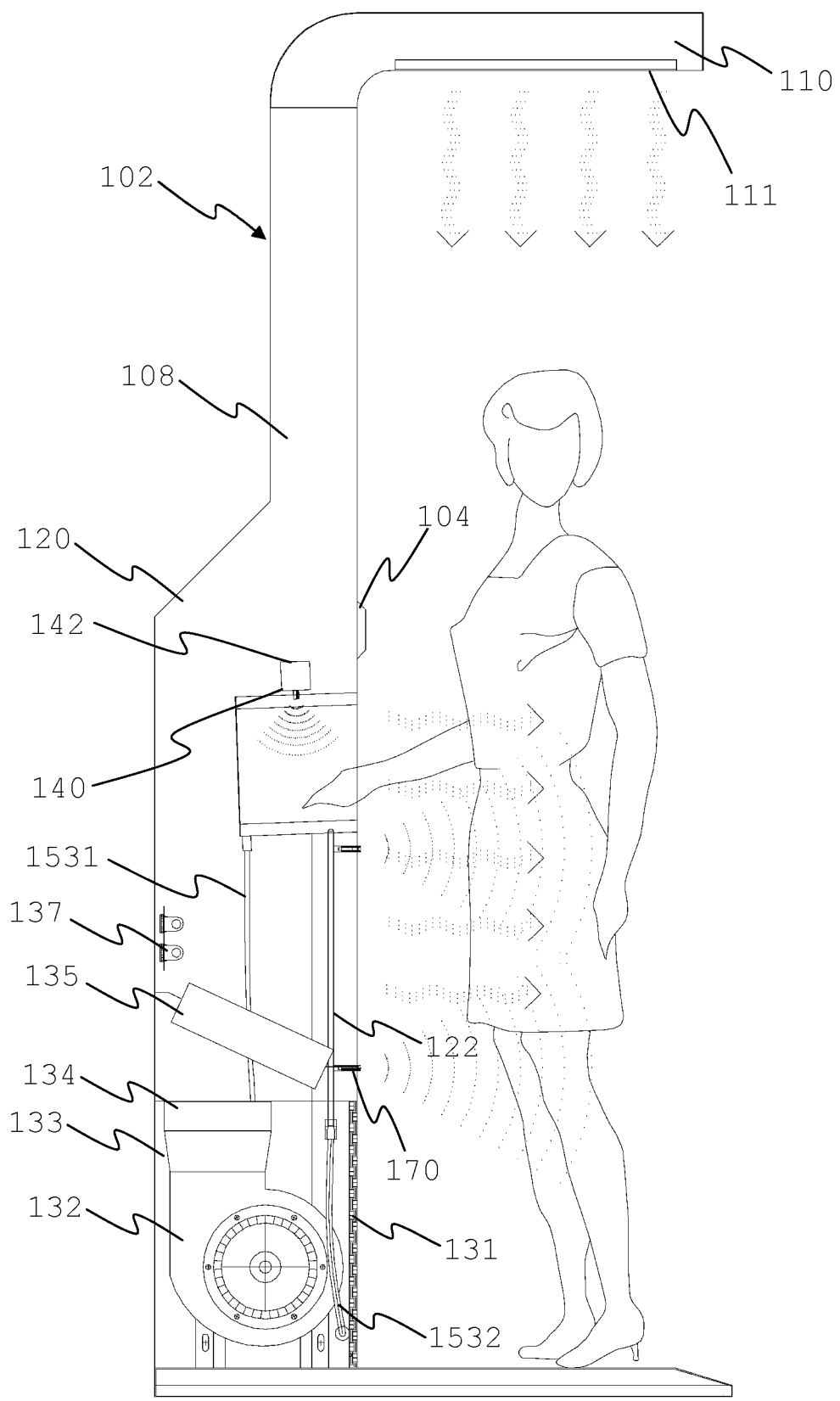
FIG. 7 shows a side view of a sanitizing apparatus according to embodiments of the present invention.

In another embodiment, a sanitizing apparatus (100) for cleaning or disinfecting, includes a booth (102) having a top portion (110) and a front portion (120). In this embodiment, an air pump (132), a filter (135), and an ultraviolet (UV) light source (137) may all be disposed in the front portion (120), as shown in FIG. 7. Further, a sanitizing solution spray unit (122) may be installed on the front portion (120) for spraying a sanitizing solution towards the user.

In this third embodiment, the front portion (120) has a set of inlets (131) and the top portion (110) has a first set of outlets (111) such that the set of inlets (131) and the first set of outlets (111) are connected to each other through a hollow inside of the front portion (120) and a hollow inside of the top portion (110). The set of inlets (131) may be constructed as a plurality of through-holes on a removable panel as in the previous embodiments.

As shown in FIG. 7, the top and front portions (110, 120) are constructed to be hollow internally and communicative with respect to each other, which forms an air passage (108) to permit internal air flow through the respective portions, the air flow preferably driven by an air pump (132). As shown, the air pump (132) is disposed in the front portion (120) of the sanitizing apparatus (100). More specifically, the air pump (132) is disposed in an air chamber (133). The air chamber (133) includes a duct (134) so that the air output from the air pump (132) is directed through the duct (134) and into the portion of the air passage (108) in the front portion (120). The air pump (132) is configured for air intake through the set of inlets (131) and send the air upwardly through the hollow inside of the front portion (120) to the hollow inside of the top portion (110) so that the air downwardly comes out of the first set of outlets (111) of the top portion (110). A filter (135) disposed above the air pump (132) filters the air output coming from the air pump (132). Preferably, the filter (135) is a high efficiency particulate air (HEPA) filter and is disposed either outside or inside of the air chamber (133) so long as the air output from the air pump (132) passes through the filter (135). For disinfecting purposes, the UV light source (137), with respect to the path of the air flow from the air pump (132), is preferably disposed after the filter (135). Alternatively, the UV light source (137) is disposed prior to the filter (135), although this configuration is less preferred because the air at this juncture will not be filtered by the filter (135). The UV light source (137) is configured to emit UV light, to disinfect the air coming out of the air pump (132) that has been filtered by the filter (135). Preferably, the UV light source (137) is a UV-C lamp. There is at least one UV light source (137) disposed in the sanitizing apparatus (100) to disinfect the air flow, preferably a plurality of UV light sources (137) as shown in FIG. 7.

Figure 8:
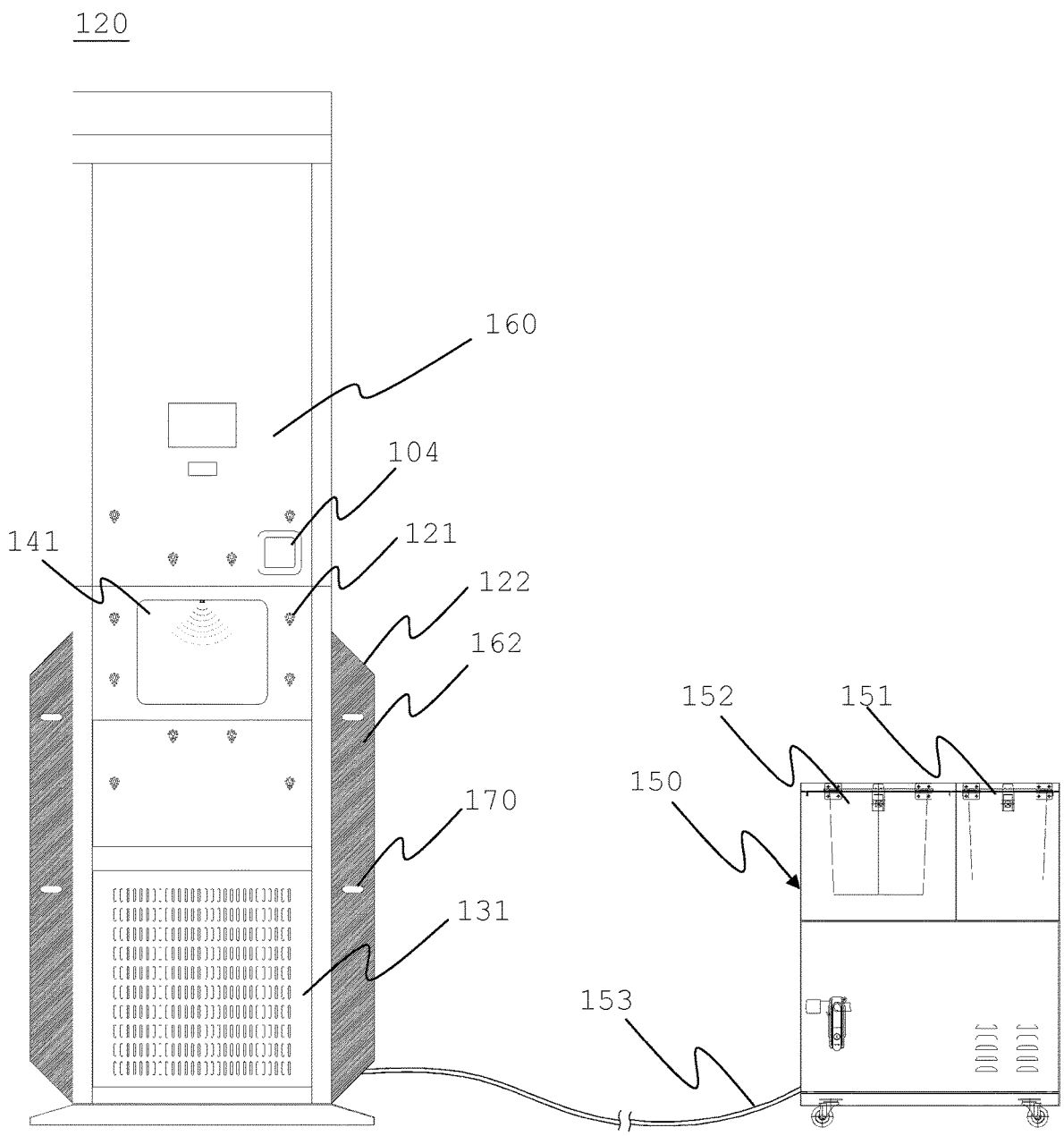
FIG. 8 shows a front view, from a user's perspective, of a front portion and an external compartment of a sanitizing apparatus according to embodiments of the present invention.

Additionally, the front portion (120) may include a second set of outlets (121) which is directed toward the user. With reference to FIGS. 7 and 8, the set of inlets (131) and second set of outlets (121) are connected to each other. Specifically, the air pump (132) takes air in through the set of inlets (131) and the filtered air comes out of the second set of outlets (121) towards the user. At the same time or thereafter, the remaining air in the air passage (108) travels to the top portion (110) where the air then passages through the set of outlets (131) provided on the top portion (110).

The hand sanitizer dispensing unit (140), disposed in the booth (102), includes a hand sanitizing compartment (141) to insert user's hands and a hand detection sensor (142) configured to detect presence of a user's hand located within the hand sanitizing compartment (141) to initiate dispensing of hand sanitizer. As in the previous embodiments, the hand detection sensor (142) detects the presence of a user's hand and is located within the hand sanitizing compartment (141). The hand detection sensor (142) may be a motion sensor configured to detect the presence of the user's hand in the hand sanitizing compartment (141) by monitoring the hand sanitizing compartment (141) for movement of the user's hand into the compartment (141) about a location where the hand sanitizer dispensing unit (140) may dispense the hand sanitizer onto the user's hand. When the hand detection sensor (142) detects the user's hand, the hand detection sensor (142) signals to the hand sanitizer dispensing unit (140) to initiate dispensing of the hand sanitizer.

The front portion (120) of the sanitizing apparatus (100) may include a front chamber (160) and a pair of flanges (162). As shown in FIG. 8, each of the flanges extends laterally from the front chamber (160). As shown, the second set of outlets (121) is disposed on the front chamber (160). The sanitizing solution spray unit (122) includes a plurality of spray nozzles (170) installed on the flanges (162). Further, the sanitizing apparatus (100) may include a contactless switch (104) configured to detect the user's hand movement in proximity for initiating spraying of the sanitizing solution to the user. When the sanitizing apparatus (100) is operative and after a user stands within it, sanitizing solution is sprayed from both flanges (162) toward the user to clean/disinfect a large portion of the front of the user. Likewise with the blowing of the air to the user, the spraying of the sanitizing solution from the spray nozzles (170) is initiated by the user placing their hand into the hand sanitizing compartment (141) such that the hand detection sensor (142) detects the user's hand inside of the hand sanitizing compartment (141), which means that the user is highly likely to be standing inside of the booth (102) area and positioned to be cleaned or disinfected from the operation of the sanitizing apparatus (100).

Figure 9A:
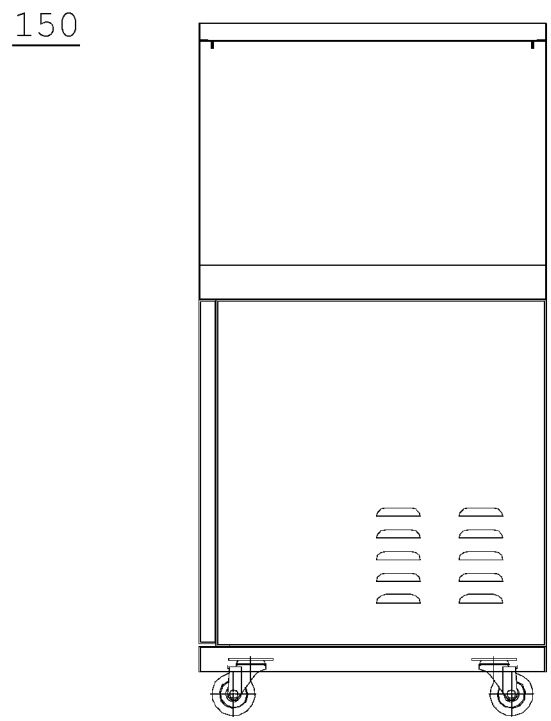
FIGS. 9A and 9B show side and inside views of an external compartment of a sanitizing apparatus according to embodiments of the present invention.
Figure 9B:
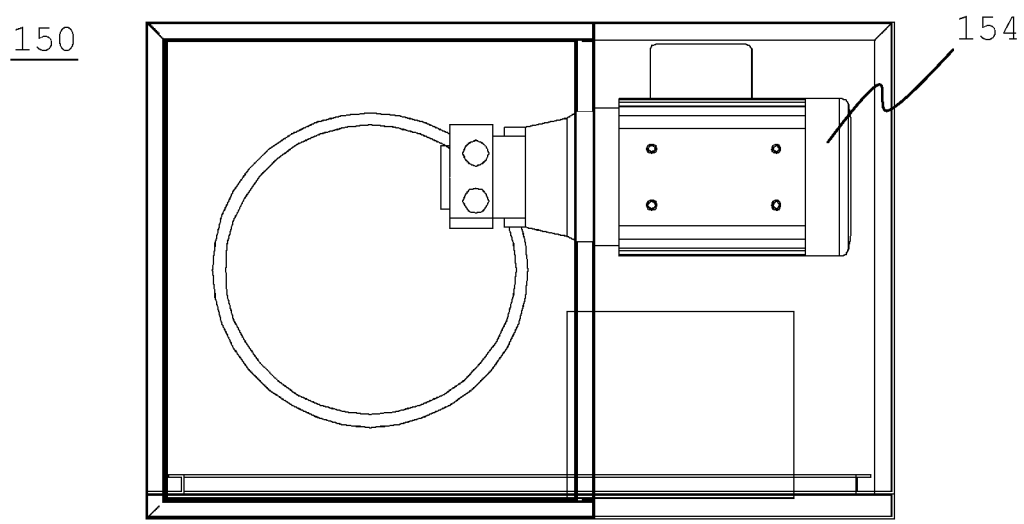

In this third embodiment, the sanitizing apparatus (100) shown in FIGS. 8 and 9A-B may further include an external compartment (150) to store first and second containers (151, 152) and a pump (154) therein. The first container (151) is provided to store the hand sanitizer that will be used by the hand sanitizer dispensing unit (140) for dispensing the hand sanitizer, and the second container (152) is provided to store the sanitizing solution to be used by the sanitizing solution spray unit (122) for spraying the sanitizing solution. With regards to the hand sanitizer, it is preferred that the hand sanitizer will contain at least 62% or more ethanol. Further, as shown in FIG. 9B, the pump (154) is disposed in the compartment (150) and is motorized to provide the pressure for dispensing the hand sanitizer and/or spraying the sanitizing solution. Preferably, the external compartment (150) is linked to the front portion (120) via a supply line (153) such that the hand sanitizer or the sanitizing solution may be respectively supplied to the hand sanitizer dispensing unit (140) or the sanitizing solution spray unit (122) via pressure that is provided to the supply line (153) by the pump (154).

The supply line (153) may be about 1 m to about 10 m in length and may be removably coupled to the pump (154) or any intermediary pipes, tubes, or adapters in between the pump (154) and the supply line (153). Additionally, the supply line (153) may include a hand sanitizer supply line (1531) to supply the hand sanitizer to the hand sanitizer dispensing unit (140) and a sanitizing solution supply line (1532) to supply the sanitizing solution to the sanitizing solution spray unit (122) as shown in FIG. 7. Alternatively, the hand sanitizer supply line (1531) may terminate at a hand sanitizer supply line adapter on a side or a back of the front portion (120). The hand sanitizer supply line adapter is constructed to serve as an intermediate connection between the hand sanitizer supply line (1531) and any piping or tubing that outputs the hand sanitizer that is supplied by the hand sanitizer supply line (1531) to the hand sanitizer dispensing unit (140). Likewise, the sanitizing solution supply line (1532) may also terminate at a sanitizing solution supply adapter on the side or the back of the front portion (120). The sanitizing solution supply adapter is constructed to serve as an intermediate connection between the sanitizing solution supply line (1532) and any piping or tubing that outputs the sanitizing solution that is supplied by the sanitizing solution supply line (1532) to the sanitizing solution spray unit (122).

A filter (155) (not shown) may be disposed between the second container (152) and the pump (154) in the external compartment (150) such that any grounds, dirt, or impurities may be filtered out from the sanitizing solution before the spraying of the sanitizing solution. Accordingly, the filter (155) may prevent clogging of any tubes and/or nozzles used for pumping and spraying the sanitizing solution. Alternatively, the filter (155) (not shown) may be disposed between the supply line (153), or more specifically the sanitizing solution supply line (1532), and the sanitizing solution spray unit (122) such that any grounds, dirt, or impurities may be filtered out from the sanitizing solution before the spraying of the sanitizing solution by the sanitizing solution spray unit (122).

For easier mobility of the external compartment (150), a plurality of casters (fixed or swiveling types) may be attached underneath the bottom portion of the compartment as shown in FIGS. 8 and 9A. Furthermore, the casters may be solid, hollow, or pneumatically filled with air or any other fill known in the art.

While the invention has been shown and described with reference to different embodiments thereof, it will be appreciated by those skilled in the art that variations in form, detail, compositions and operation may be made without departing from the spirit and scope of the invention as defined by accompanying claims.

What is claimed is:

1. A sanitizing apparatus for cleaning or disinfecting a user, comprising:
   a booth having a top portion, a front portion and a rear portion, wherein the rear portion has a set of inlets and the top portion has a first set of outlets such that the set of inlets and the first set of outlets are connected to each other through a hollow inside of the rear portion and a hollow inside of the top portion, wherein the set of inlets faces the front portion;
an air pump disposed in the rear portion wherein the air pump takes air in through the set of inlets and sends the air upwardly through the hollow inside of the rear portion to the hollow inside of the top portion so that the air downwardly comes out of the first set of outlets of the top portion;
a filter disposed in the rear portion over the air pump wherein the filter filters the air coming out of the air pump;
a ultraviolet (UV) light source disposed in the rear portion over the air pump wherein the UV light source emits UV light for disinfecting the air coming out of the air pump; and
a sanitizing solution spray unit installed on the front portion for spraying a sanitizing solution towards the user and the rear portion,
wherein the sanitizing solution is sprayed from the front portion towards the user and the rear portion such that a sanitizing curtain is formed to attenuate any outside spread of germs and/or dust from the sanitizing apparatus,
wherein a range of the sprayed sanitizing solution is limited to about below an upper respiratory tract of the user.

2. The sanitizing apparatus of claim 1, further comprising a hand sanitizer dispensing unit for dispensing a hand sanitizer.

3. The sanitizing apparatus of claim 2, wherein the hand sanitizer dispensing unit is disposed in the front portion,
wherein the hand sanitizer dispensing unit comprises a hand sanitizing compartment to insert user's hands and a hand detection sensor configured to detect presence of a user's hand located within the hand sanitizing compartment to initiate dispensing of hand sanitizer.

4. The sanitizing apparatus of claim 2, further comprising a first container for storing the hand sanitizer for dispensing the hand sanitizer, and
wherein the first container is disposed in the front portion.

5. The sanitizing apparatus of claim 4, further comprising a second container for storing the sanitizing solution and a pump for spraying the sanitizing solution,
wherein the pump is disposed in the front portion and the second container is disposed in the front portion over the pump,
wherein the sanitizing apparatus comprises a compartment to store the first and second containers therein.

6. The sanitizing apparatus of claim 1, further comprising a second container for storing the sanitizing solution and a pump for spraying the sanitizing solution,
wherein the pump is disposed in the front portion and the second container is disposed in the front portion over the pump.

7. The sanitizing apparatus of claim 1, wherein the front portion comprises a second set of outlets which is directed toward the rear portion,
wherein the set of inlets and second set of outlets are connected to each other through the hollow inside of the rear portion, the hollow inside of the top portion, and a hollow inside of the front portion,
wherein the air pump takes air in through the set of inlets and sends the air upwardly through the hollow inside of the rear portion to the hollow inside of the top portion and then downwardly to the hollow inside of the front portion so that the air comes out of the second set of outlets towards the rear portion.

8. The sanitizing apparatus of claim 7, wherein the front portion comprises a front chamber and a pair of flanges, each of which extends from the front chamber,
wherein the second set of outlets is disposed on the front chamber,
wherein the sanitizing solution spray unit comprises a plurality of spray nozzles installed on the flanges.

9. The sanitizing apparatus of claim 1, further comprising a contactless switch configured to detect the user's hand movement in proximity for initiating spraying of the sanitizing solution to the user.

10. The sanitizing apparatus of claim 9, further comprising a user detection sensor to detect presence of the user for initiating air circulation from the set of inlets to the first set of outlets by the air pump.

11. The sanitizing apparatus of claim 1, wherein air passage in the rear portion is narrower in an upper part of the rear portion than a lower part of the rear portion,
wherein the filter is slanted towards the user and the UV light source is disposed on an outer side wall of the rear portion right over the filter.

12. The sanitizing apparatus of claim 1, wherein the filter is a high efficiency particulate air (HEPA) filter,
wherein the UV light source is a UV-C lamp.

13. The sanitizing apparatus of claim 1, wherein the air pump includes a prefilter installed on the set of inlets.

14. The sanitizing apparatus of claim 8, wherein the sanitizing solution is sprayed from the flanges of the front portion.

15. A sanitizing apparatus for cleaning or disinfecting a user, comprising:
a booth having a set of inlets and a set of outlets wherein the set of inlets and the set of outlets are connected to each other by hollow inside of the booth;
an air pump disposed in the booth wherein the air pump takes air in through the set of inlets and sends the air through the hollow inside of the booth so that the air comes out of the set of outlets of the booth;
a filter disposed in the booth over the air pump wherein the filter filters the air coming out of the air pump;
a ultraviolet (UV) light source disposed in the booth over the air pump wherein the UV light source emits UV light for disinfecting the air coming out of the air pump;
a sanitizing solution spray unit installed on the booth for spraying a sanitizing solution to the user; and
a hand sanitizer dispensing unit disposed in the booth for dispensing a hand sanitizer,
wherein the sanitizing solution is sprayed from the booth towards the user such that a sanitizing curtain is formed to attenuate any outside spread of germs and/or dust from the sanitizing apparatus,
wherein a range of the sprayed sanitizing solution is limited to about below an upper respiratory tract of the user.

16. The sanitizing apparatus of claim 15, wherein the hand sanitizer dispensing unit comprises a hand sanitizing compartment to insert user's hands and a hand detection sensor configured to detect presence of a user's hand located within the hand sanitizing compartment to initiate dispensing of hand sanitizer.

17. The sanitizing apparatus of claim 15, wherein the booth comprises a side chamber and a pair of flanges, each of which extends from the side chamber,
wherein the sanitizing solution spray unit comprises a plurality of spray nozzles installed on the flanges.

18. The sanitizing apparatus of claim 17, wherein the set of outlets is formed on the side chamber and a top portion of the booth.

19. The sanitizing apparatus of claim 15, wherein air passage in a side portion of the booth is narrower in an upper part of the side portion than a lower part of the side portion,
wherein the filter is slanted towards the user and the UV light source is disposed on an outer side wall of the side portion right over the filter.

20. The sanitizing apparatus of claim 15, wherein the filter is a high efficiency particulate air (HEPA) filter.

\* \* \* \* \*